United States Patent [19]

Eurkart et al.

[11] Patent Number: 4,826,829
[45] Date of Patent: May 2, 1989

[54] 2-SUBSTITUTED ETHYNYL THIOPHENE PESTICIDES

[75] Inventors: Susan E. Eurkart, Trenton, N.J.; Richard B. Phillips, Riverbank, Calif.; David M. Roush, Princeton, N.J.

[73] Assignee: FMC Corporation, Philadelphia, Pa.

[21] Appl. No.: 169,110

[22] Filed: Mar. 9, 1988

Related U.S. Application Data

[63] Continuation-in-part of Ser. No. 889,040, Jul. 23, 1986, abandoned.

[51] Int. Cl.$^4$ .................. A01N 43/02; C07D 409/00; C07D 333/12; C07D 333/22
[52] U.S. Cl. ......................... 514/95; 549/59; 549/74; 549/76; 549/78; 549/79; 549/80; 549/77; 549/6; 514/438; 514/444
[58] Field of Search ............... 549/59, 74, 75, 76, 549/78, 79, 80, 83, 77, 6; 514/438, 444, 95

[56] References Cited

PUBLICATIONS

Hakimelahi, et al., Tetrahedron Lett., 38, 3643 (1979).
Mori, et al., Agric. Biol. Chem., 46, 309 (1962).
Schulte, et al., Ber., 95, 1943 (1962).
Takahashi, et al., Synthesis, 627 (1980).
Tamao, et al., Tetrahedron, 38, 3347 (1982).
Cadogan "Organo Phosphorus Reagents in Organic Synthesis" Academic Press, New York, New York, 1979, p. 155.
Angew. Chem., 72, 920 (1960).
Chem. Abstr., 98, 29640t (1983).
Chem. Abstr., 59, 7522h (1963).
Org. Syn. Coll. vol. II, p. 357 (1950).
J. Chem. Soc., C, 89 (1966).

Primary Examiner—Mary C. Lee
Assistant Examiner—Robert C. Whittenbaugh
Attorney, Agent, or Firm—Robert L. Anderson; H. Robinson Ertelt

[57] ABSTRACT

Thiophene derivatives of the following formula are effective as acaricdies:

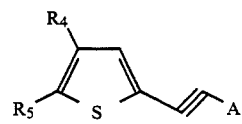

wherein
A is selected from -phenylthienyl and -phenyl optionally carrying one or more substitutents selected from -lower alkyl, -lower alkoxy, -phenoxy, -hydroxy, -halogen, -lower haloalkyl, -phenylcarbonyl, -lower alkyl carbonyloxy, -lower alkyl sulfonyl, -lower alkyl sulfonyloxy, -amino, -lowr alkyl carboxamido, and -lower haloalkyl carboxamido;
$R_4$ is selected from -hydrogen and -lower alkyl; and
$R_5$ is selected from -thienyl optionally carrying one or more substituents selected from -lower alkyl, -phenylethynyl, -lower alkylthio, -lower haloalkyl carbonyl, and lower alkyl sulfoxy; or -phenyl optionally carrying one or more substituents selected from -lower alkyl and -lower alkoxy.

5 Claims, No Drawings

2-SUBSTITUTED ETHYNYL THIOPHENE PESTICIDES

This application is a continuation-in-part of application Ser. No. 889,040, filed on 7-23-86, now abandoned.

This invention is in the field of heterocyclic organic chemical compounds which contain a thiophene nucleus. More particularly, the invention includes certain thiophene compounds per se, agricultural compositions containing the novel compounds, and the method of using a broad class of such compounds to control agricultural pests.

There is increasing scientific evidence that toxic reactions initiated by light play an important role in natural control of insect populations. In the last few years the concept of using photoactive agents as insecticides has been advanced. Such photosensitizers typically display insecticidal activity by catalyzing the electronic triplet to singlet conversion of molecular oxygen. The excited singlet oxygen behaves as a superoxidizing agent, destroying the insect tissues which it contacts, hence killing the insect.

According to the present invention, 2-substituted ethynyl thiophene compounds of the following structural formula are photodynamic insecticides and acaricides:

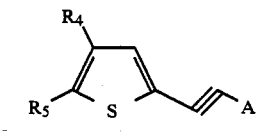

wherein
A is selected from (a) thienyl carrying a substituent selected from halogen, phenyl, alkoxycarbonyl or phenyl; (b) naphthyl; and (c) phenyl optionally carrying one or more substituents selected from lower alkyl, lower alkoxy, phenoxy, halogen, hydroxy, formyl, lower haloalkyl, phenylcarbonyl, lower alkyl carbonyloxy, lower alkyl sulfonyl, lower alkyl sulfonyloxy, amino, lower alkylcarbonylamino, lower haloalkylcarbonylamino, haloalkoxy, and haloalkoxyalkyl.
$R_4$ is selected from -hydrogen and -lower alkyl; and $R^5$ is selected from (a) thienyl optionally carrying one or more substituents selected from lower alkyl, phenylethynyl, lower alkylthio, lower haloalkylcarbonyl, lower alkyl sulfinyl, halogen, lower alkoxycarbonyl, cycloalkoxycarbonyl and O,O-dialkylphosphoryl; (b) naphthyl; and (c) phenyl optionally carrying one or more substituents selected from lower alkyl, lower alkoxy, halogen and alkoxycarbonyl.

In the aforesaid description and wherever the terms appear hereinafter, "halo" and "halogen" mean fluorine, chlorine or bromine. The term "lower" modifying "alkyl," "alkoxy," and the like, implies a straight or branched hydrocarbon chain of 1-6, preferably 1-4, carbon atoms. "Halo" modifying "alkyl", "alkoxy", and the like means one or more hydrogen atoms have been replaced with halogen.

Among the aforesaid compounds, it is preferred that A is -phenyl or -phenyl carrying a -lower alkyl or -halogen substituent; $R_4$ is -hydrogen; and $R_5$ is -phenyl or -thienyl optionally carrying a -lower alkyl substituent. Specific preferred compounds include 1-(5-phenylthien-2-yl)-2-phenylethyne, 1-[5'-methyl(2,2'-bithien-5-yl)]-2-phenylethyne, 1-[5'-methyl(2,2'-bithien-5-yl]-2-[4-(1-methylethyl)phenyl]ethyne, 1-(5-phenylthien-2-yl)-2-(4-methylphenyl)ethyne, and 1-[5'-methyl(2,2'-bithien-5-yl)]-2-(4-chlorophenyl)ethyne.

The 2-substituted ethynyl thiophene compounds of this invention are prepared by general techniques which form part of the prior art. For example, attention is directed to Takahashi, et al., *Synthesis*, 627 (1980); Minnis, *Org. Syn.* Coll. Vol. II, p. 357; Cadogan, "Organo Phosphorus Reagents in Organic Synthesis," Academic Press, New York, NY, 1979, p. 155; Tomao, et al., *Tetrahedon*, 38, 3347 (1982); and Hakimelahi, et al., *Tet. Lett.*, 38, 3643 (1979). These techniques are illustrated by the following specific examples:

EXAMPLE 2

1-(5-Phenylthien-2-yl)-2-(4-chlorophenyl)ethyne

Under a nitrogen atmosphere, a mixture of 0.7 gram (catalyst) of bis(1,3-diphenylphosphino)propanenickel (II) chloride in 200 mL of dry diethyl ether was stirred, and 40 grams (0.245 mole) of 2-bromothiophene was added. The mixture was cooled to 0° C., and 113 mL (0.328 mole) of phenylmagnesium bromide (3M in diethyl ether) was added during a 20 minute period. Upon completion of addition, the reaction mixture was allowed to warm to ambient temperature and then was heated under reflux for 16 hours. The reaction mixture was poured with shaking into 500 mL of an aqueous 10% hydrochloric acid solution. The organic layer was separated and washed with distilled water. The organic layer was dried with magnesium sulfate and filtered. The filtrate was concentrated under reduced pressure to a residue. The residue was distilled under vacuum to yield 36 grams of 2-phenylthiophene; b.p. 140° C./3 mm, as a low melting solid.

Under a nitrogen atmosphere 35 mL of dimethylformamide was cooled to 0° C. and 7 mL of phosphorus oxychloride was added with stirring. The solution was allowed to warm to ambient temperature, and then a solution of 10.0 grams (0.0625 mole) of 2-phenylthiophene in 10 mL of dimethylformamide was added in one portion. The reaction mixture was heated to 80° C. where it stirred for 24 hours and then poured into 250 mL of an aqueous 10% sodium hydroxide solution containing 50 grams of ice. The resulting slurry was extracted with diethyl ether, and the extract was washed in succession with water, an aqueous solution saturated with sodium chloride, and water. The organic layer was concentrated under reduced pressure to a solid residue which was dried under high vacuum to yield 6.8 grams of 5-formyl-2-phenylthiophene.

Under a nitrogen atmosphere a stirred solution of 6.7 grams (0.067 mole) of di(1-methylethyl)amine in 50 mL of tetrahydrofuran was cooled to −78° C., and 29 mL (0.0725 mole) of n-butyllithium (2.5M in hexanes) was added. Upon completion of addition the reaction mixture was stirred at −78° C. for 15 minutes. The reaction mixture was warmed to 0° C. where it stirred for 30 minutes, and then 15.1 grams (0.0575 mole) of diethyl (4-chlorophenyl)methylphosphonate was added. The reaction mixture was cooled to −78° C. In a second reaction vessel under a nitrogen atmosphere, a rapidly stirred solution of 11.4 grams (0.068 mole) of trifluoromethanesulfonyl chloride in 60 mL of tetrahydrofuran was cooled to −78° C., and the cold phosphonate solution prepared above was added. Upon completion of addition the reaction mixture was allowed to warm to ambient temperature where it stirred for 16 hours. The reaction mixture was stirred with aqueous ammonium chloride solution to quench any further reaction. The organic layer was taken up in diethyl ether and was washed first with an aqueous ammonium chloride solution and then with an aqueous sodium chloride solution. The organic layer was dried with magnesium sulfate and filtered through diatomaceous earth. The filtrate was concentrated under reduced pressure to a residue. The residue was subjected to column chromatography on silica gel. Elution was accomplished using 10% ethyl acetate in hexane. The appropriate fractions were combined and concentrated under reduced pressure to yield 8.9 grams of diethyl (4-chlorophenyl)chloromethylphosphonate.

A solution of 1.3 grams (0.007 mole) of 5-formyl-2-phenylthiophene and 2.0 grams (0.007 mole) of diethyl (4-chlorophenyl)chloromethylphosphonate in 30 mL of dimethylformamide was stirred, and 0.5 gram (0.009 mole) of sodium methoxide was added. The reaction mixture was stirred at ambient temperature for 18 hours, and then was quenched with an aqueous solution saturated with ammonium chloride. The reaction mixture was cooled and filtered to collect a solid. The solid was dried to yield 2.0 grams of 1-(5-phenylthien-2-yl)-2-chloro-2-(4-chlorophenyl)ethene. The intermediate ethene, 1.2 grams (0.004 mole), was treated with 0.6 gram (0.005 mole) of potassium tert-butoxide in 20 mL of tetrahydrofuran. The reaction mixture was heated under reflux for four hours and then was allowed to cool to ambient temperature during a 16 hour period. An excess of aqueous 1.2N hydrochloric acid was slowly added to the reaction mixture, followed by an excess of an aqueous solution saturated with ammonium chloride. The reaction mixture was cooled, and a solid was collected by filtration. The solid was dried to yield 1.1 grams of 1-(5-phenylthien-2-yl)-2-(4-chlorophenyl)ethyne; m.p. 141°–145° C. The nmr spectrum was consistent with the proposed structure.

EXAMPLE 11

1-[5'-Methyl(2,2'-bithien-5-yl)]-2-[4-(1-methylethyl)phenyl]ethyne

Under a nitrogen atmosphere a stirred solution of 32.0 grams (0.193 mole) of 2,2'-bithienyl in 150 mL of diethyl ether was cooled to −5°0 C., and 90.5 mL (0.226 mole—2.6M in hexanes) of n-butyllithium was added slowy dropwise. Upon completion of addition the reaction mixture was stirred at −5° C. for one hour, and then a solution of 27.8 grams (0.220 mole) of dimethylsulfate in 75 mL of diethyl ether was added very slowly dropwise. Upon completion of addition the reaction mixture was allowed to warm to ambient temperature where it stirred for 18 hours. After this time the reaction mixture was poured into 350 mL of an aqueous 10% ammonium chloride solution. The mixture was extracted with diethyl ether, and the combined extracts were washed with water. The organic layer was dried with magnesium sulfate and filtered. The filtrate was concentrated under reduced pressure to a residual oil. The oil was distilled under reduced pressure to yield 30.0 grams of 5-methyl(2,2'-bithienyl); b.p. 108°–113° C./1.9 mm.

A solution of 12.2 grams (0.068 mole) of 5-methyl(2,2'-bithienyl) in 50 mL of heptane was stirred, and, in alternate portions, 17.8 (0.070 mole) of iodine and 12.4 grams (0.057 mole) of mercury (II) oxide were added. Upon completion of addition the reaction mixture stirred for 20 hours, and then was filtered through diatomaceous earth. The filtrate was concentrated under reduced pressure to a residual solid. The solid was recrystallized from ethanol to yield 5.2 grams of 5-iodo-5'-methyl(2,2'-bithienyl).

A solution of 10 grams (0.050 mole) of 4-(1-methylethyl)bromobenzene and 8.4 grams (0.10 mole) of 1,1-dimethyl-2-propyn-1-ol in 75 mL of triethylamine was stirred, and 0.7 gram (0.001 mole) of bis(triphenylphosphine)palladium(II) chloride and 0.2 gram (0.001 mole) of copper (I) iodide were added. Upon completion of addition the reaction mixture was heated under reflux for four hours. The reaction mixture was cooled and concentrated under reduced pressure to a residue. The residue was dissolved in diethyl ether and was washed first with an aqueous 10% ammonium chloride solution, then with water. The organic layer was dried with magnesium sulfate and filtered. The filtrate was concentrated under reduced pressure to a residual oil. The oil was dissolved in 100 mL of toluene, 4.0 grams of sodium hydroxide was added to the solution, and the mixture was heated under reflux for four hours. The mixture was allowed to cool to ambient temperature where it stood for 18 hours. After this time the mixture was concentrated under reduced pressure to a residual oil. The oil was subjected to column chromatography on silica gel. Elution was accomplished with 1–20% chloroform in hexane. The appropriate fractions were combined and concentrated under reduced pressure to yield 2.4 grams of 4-(1-methylethyl)phenylethyne as an oil. The nmr spectrum was consistent with the proposed structure.

Under a nitrogen atmosphere, a solution of 1.0 gram (0.007 mole) of 4-(1-methylethyl)phenylethyne and 2.1 grams (0.007 mole) of 5-iodo-5'-methyl(2,2'-bithienyl) in 45 mL of triethylamine was stirred, and 0.1 gram (0.14 mole) of bis(triphenylphosphine)palladium(II) chloride and 0.03 gram (0.16 mole) of copper (I) iodide were added. Upon completion of addition the reaction mixture was stirred for 72 hours and then poured into an aqueous 10% ammonium chloride solution. The mixture was extracted with 400 mL of chloroform. The extract was washed with water, dried with magnesium sulfate, and then filtered. The filtrate was concentrated under reduced pressure to a residue. The residue was subjected to column chromatography on silica gel. Elution was accomplished with hexane. The appropriate fractions were combined and concentrated under reduced pressure to yield 0.85 gram of 1-[5'-methyl(2,2'-bithien-5-yl)]-2-[4-(1-methylethyl)phenyl]ethyne; m.p. 92°–92.5° C. The nmr spectrum was consistent with the proposed structure.

The following additional compounds were prepared by similar techniques, their identity being confirmed by nmr spectra.

| Example | Name | Melting Point (°C.) |
| --- | --- | --- |
| 1 | 1-(5-phenylthien-2-yl)-2-phenylethyne | 115–118 |
| 3 | 1-(5-phenylthien-2-yl)-2-[4-(1-methylethyl)phenyl]ethyne | 98–99 |
| 4 | 1-(5-phenylthien-2-yl)-2-[4-(1-methylethoxy)phenyl]ethyne | 115–116 |
| 5 | 1-(5-phenylthien-2-yl)-2-(4-phenoxyphenyl)ethyne | 111–113 |
| 6 | 1-(5-phenylthien-2-yl)-2-(4-amino- | 156–158 |

-continued

| Example | Name | Melting Point (°C.) |
|---|---|---|
| 7 | 1-(5-phenylthien-2-yl)-2-(4-acetylaminophenyl)ethyne | 198–200 |
| 8 | 1,2-bis(3,4-dimethyl-5-phenylthien-2-yl)ethyne | 75–78 |
| 9 | 1-(2,2'-bithien-5-yl)-2-phenylethyne | 84–85 |
| 10 | 1-[5'-methyl(2,2'-bithien-5-yl)]-2-phenylethyne | 84–85 |
| 12 | 1-[5'-methyl(2,2'-bithien-5-yl)]-2-(4-trifluoromethylphenyl)ethyne | 146–147 |
| 13 | 1-[5'-methyl(2,2'-bithien-5-yl)]-2-(4-formylphenyl)ethyne | 155–156 |
| 14 | 1-[5'-methyl(2,2'-bithien-5-yl)]-2-(4-benzoylphenyl)ethyne | 173–174 |
| 15 | 1-[5'-methyl(2,2'-bithien-5-yl)]-2-[3-(methylsulfonyloxy)phenyl]ethyne | 127–128 |
| 16 | 1-[5'-methyl(2,2'-bithien-5-yl)]-2-[4-(acetyloxy)phenyl]ethyne | 108–109 |
| 17 | 1-(5-phenylthien-2-yl)-2-(4-methylphenyl)ethyne | 136–137 |
| 18 | 1-(5-phenylthien-2-yl)-2-(2-methylphenyl)ethyne | 87–88 |
| 19 | 1-[5'-methyl(2,2'-bithien-5-yl)]-2-[4-(methylsulfonyl)phenyl]ethyne | 180–182 |
| 20 | 1-(5-phenylthien-2-yl)-2-(3-methylphenyl)ethyne | 115–116 |
| 21 | 1-[5-(4-methoxyphenyl)thien-2-yl]-2-phenylethyne | 135–136 |
| 22 | 1-[5-[3-(1-methylethyl)phenyl]thien-2-yl]-2-phenylethyne | oil |
| 23 | 5,5'-bis(2-phenylethynyl)-(2,2'-bithienyl) | 171–172 |
| 24 | 1-[4-methyl-5-(3-methylphenyl)-thien-2-yl]-2-phenylethyne | oil |
| 25 | 1-[5'-methyl(2,2'-bithien-5-yl)]-2-(4-hydroxyphenyl)ethyne | 139–140 |
| 26 | 1-[5'-(trifluoroacetyl)-(2,2'-bithien-5-yl)]-2-phenylethyne | 140–141 |
| 27 | 1-[5'-(methylsulfinyl)(2,2'-bithien-5-yl)]-2-[4-(1-methylethyl)phenyl]ethyne | 144–146 |
| 28 | 1-[5-(4-pentoxyphenyl)thien-2-yl]-2-phenylethyne | 94–95 |
| 29 | 1-[5'-methyl(2,2'-bithien-5-yl)]-2-[4-(methylsulfonyloxy)phenyl]ethyne | 147–148 |
| 30 | 1-(5-phenylthien-2-yl)-2-[2-(1-methylethyl)phenyl]ethyne | oil |
| 31 | 1-(5-phenylthien-2-yl)-2-(4-fluorophenyl)ethyne | 118–120 |
| 32 | 1-[5'-methyl(2,2'-bithien-5-yl)]-2-(4-ethoxyphenyl)ethyne | 109–110 |
| 33 | 1-(5-phenylthien-2-yl)-2-(2-aminophenyl)ethyne | 130–132 |
| 34 | 1-(5-phenylthien-2-yl)-2-(2-fluorophenyl)ethyne | 96–97 |
| 35 | 1-(5-phenylthien-2-yl)-2-[2-(trifluoromethylcarbonylamino)phenyl]ethyne | 134–134.5 |
| 36 | 1-[5'-methyl(2,2'-bithien-5-yl)]-2-(4-chlorophenyl)ethyne | 140–142 |
| 37 | 1-[5'-methylthio(2,2'-bithien-5-yl)]-2-[4-(1-methylethyl)phenyl]ethyne | 96–99 |

EXHBIT A

| Example | Name | Melting Point (°C.) |
|---|---|---|
| 38 | 1-[5'-(O,O—diethylphosphoryl)(2,2'-bithien-5-yl)]-2-(2-methylphenyl)ethyne | 82–83 |
| 39 | 1-[5-(4-Fluorophenyl)thien-2-yl]-2-phenylethyne | |
| 40 | 1-(5-Phenylthien-2-yl)-2-(4-methoxyphenyl)ethyne | 124–125 |
| 41 | 1-[5'-Iodo(2,2'-bithien-5-yl)]-2-phenylethyne | 128–129 |
| 42 | 1-[5'-Ethoxycarbonyl(2,2'-bithien-5-yl)]-2-phenylethyne | 97–98 |
| 43 | 1-(5-Phenylthien-2-yl)-2-(thien-2-yl)ethyne | 117–119 |
| 44 | 1-(5-Phenylthien-2-yl)-2-(3-aminophenyl)ethyne | 114–115 |
| 45 | 1-(5-Phenylthien-2-yl)-2-(4-trifluoromethoxyphenyl)ethyne | 101–102 |
| 46 | 1-[5-(4-Chlorophenyl)thien-2-yl]-2-phenylethyne | Solid |
| 47 | 1-[5-(4-methylphenyl)thien-2-yl]-2-phenylethyne | Solid |
| 48 | 1-[5-(3-Methylphenyl)thien-2-yl]-2-phenylethyne | 57–58 |
| 49 | 1-(5-Phenylthien-2-yl)-2-(4-ethoxyphenyl)ethyne | 110–111 |
| 50 | 2,5-bis[2-[4-ethoxyphenyl]-ethynyl]thiophene | 121–123 |
| 51 | 1-(5-Phenylthien-2-yl)-2-[4-(2-fluoroethoxy)phenyl]ethyne | 129–130 |
| 52 | 1-[5-(Naphth-1-yl)thien-2-yl]-2-phenylethyne | 135–136 |
| 53 | 1-[5'-Methoxycarbonyl(2,2'-bithien-5-yl)]-2-phenylethyne | 149–150 |
| 54 | 1-[5'-[(1-Methylethoxy)carbonyl](2,2'-bithien-5-yl)]-2-phenylethyne | 85–86 |
| 55 | 1-[5'-Cyclohexoxycarbonyl(2,2'-bithien-5-yl)]-2-phenylethyne | 89–90 |
| 56 | 1-(5-Phenylthien-2-yl)-2-(5-iodothien-2-yl)ethyne | 124–125 |
| 57 | 3-Methyl-2,5-bis(2-phenylethynyl)-thiophene | 109–110 |
| 58 | 1-(5-Phenylthien-2-yl)-2-(5-ethoxycarbonylthien-2-yl)ethyne | 102–103 |
| 59 | 1-(5-Phenylthien-2-yl)-2-[4-(2-fluoroethoxymethyl)phenyl]ethyne | 93–94.5 |
| 60 | 1-[5'-Methyl(2,2'-bithien-5-yl)]-2-(4-propoxyphenyl)ethyne | 114–115 |
| 62 | 1-(5-Phenylthien-2-yl)-2-(naphth-1-yl)ethyne | 59–60 |
| 63 | 1-(5-Phenylthien-2-yl)-2-(2-trifluoromethylphenyl)ethyne | 50–51.5 |
| 64 | 1-(5-Phenylthien-2-yl)-2-(5-fluoro-2-methylphenyl)ethyne | 117–118 |
| 65 | 1-[5'-Methyl(2,2'-bithien-5-yl)]-2-(2-methylphenyl)ethyne | 77–78 |
| 66 | 2,5-bis(2-Phenylethynyl)thiophene | 80–81 |
| 67 | 1-[5'-Ethoxycarbonyl(2,2'-bithien-5-yl)]-2-(2-methylphenyl)ethyne | 105–106 |
| 68 | 1-(5-Phenylthien-2-yl)-2-(3-methoxyphenyl)ethyne | 71–72 |

In the normal use of the insecticidal and acaricidal thienyl compounds of the present invention, the thienyl compounds usually will not be employed free from admixture or dilution, but ordinarily will be used in a suitable formulated composition compatible with the method of application and comprising an acaricidally effective amount of thienyl compound. The thienyl compounds of this invention, like most pesticidal agents, may be blended with the agriculturally acceptable surface-active agents and carriers normally employed for facilitating the dispersion of active ingredients, recognizing the accepted fact that the formulation and mode of application of an acaricide may affect the activity of the material. The present thienyl compounds may be applied, for example, as sprays, dusts, or granules to the area where pest control is desired, the type of application varying of course with the pest and the environment. Thus, the thienyl compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the thienyl compounds. The granule particles are relatively large, a diameter of about 400–2500 microns typically. The particles are either impregnated with the thienyl compound from solution or coated with the thienyl compound, adhesive sometimes being employed. Granules generally contain 0.05–10%, preferably 0.5–5%, active ingredient as the acaricidally effective amount.

Dusts are admixtures of the thienyl compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the acaricide. These finely divided solids have an average particle size of less than about 50 microns. A typical dust formulation useful for controlling acarids contains 1 part of thienyl compound, such as 1-[5'-methyl(2,2'-bithien-5-yl)]-2-[4-(1-methylethyl)-phenyl]ethyne, and 99 parts of talc.

The thienyl compounds of the present invention may be made into liquid concentrates by dissolution or emulsification in suitable liquids and into solid concentrates by admixture with talc, clays, and other known solid carriers used in the pesticide art. The concentrates are compositions containing, as an acaricidally effective amount, about 5–50% thienyl compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of 1-[5'-methyl(2,2'-bithien-5-yl)]-2-[4-(1-methylethyl)phenyl]ethyne, 22.0% attapulgite diluent, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A solid concentrate formulation useful for controlling acarids contains 1.5 parts each of sodium lignosulfonate and sodium lauryl-sulfate as wetting agents, 25 parts of 1-[5'-methyl(2,2'-bithien-5-yl)]-2-[4-(1-methylethyl)]ethyne, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the thienyl compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of 1-[5'-methyl(2,2'-bithien-5-yl)]-2-[4-(1-methylethyl)phenyl]ethyne; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the acaricidal composition.

Other useful formulations include simple solutions of the active ingredient in a solvent in which it is completely soluble at the desired concentration, such as acetone or other organic solvents.

An insecticidally or acaricidally effective amount of thienyl compound in an insecticidal or acaricidal composition diluted for application is normally in the range of about 0.001% to about 8% by weight. Many variations of spraying and dusting compositions known in the art may be used by substituting the thienyl compounds of this invention into compositions known or apparent in the art.

The insecticidal or acaricidal compositions of this invention may be formulated with other active ingredients, including other acaricides, nematicides, insecticides, fungicides, plant growth regulators, fertilizers, etc. In using the compositions to control acarids, it is only necessary that an insecticidally or acaricidally effective amount of thienyl compound be applied to the locus where control is desired. Such locus may, e.g., be the acarids themselves, plants upon which the acarids feed, or the acarid habitat. When the locus is soil, e.g., soil in which agricultural crops are or will be planted, the active compound may be applied to and optionally incorporated into the soil. For most applications, an insecticidally or acaricidally effective amount will be about 50 to 750 g per hectare, preferably 150 g to 500 g per hectare.

The acaricidal activity of the thienyl compounds whose preparation is described above was evaluated as follows:

The thienyl compounds were tested for acaricidal activity under near ultraviolet light (wavelength 340–360 nanometers) at an intensity of 1600–2400 microwatts/$cm^2$ using test procedures adapted to the organisms in the test. Regardless of the organism, foliage of whole plants or foliage removed from whole plants was sprayed to runoff with a 10% acetone-0.25% octylphenoxypolyethoxyethanol-water solution containing up to 250 ppm of the test compound.

Leaves infested with adult twospotted spider mites (*Tetranychus urticae*) were removed from culture plants and cut into segments containing 50–75 female mites. Each segment was placed on the upper leaf surface of a whole pinto bean (*Phaseolus vulgaris*) plant. After the mites had migrated to the under surfaces of the leaves, the leaf segments used to infest were removed and each plant sprayed with test chemical as described above. After the plants had dried, the entire plant and pot were placed in metal trays in a hood. A supply of water in the tray kept the plants turgid. Tests were conducted against both susceptible and phosphate resistant strains.

The test results were collected and recorded at the end of a 24 hour or 48 hour exposure period. The data obtained under ultraviolet irradiation appear in Table 1.

2-Substituted ethynyl thiophene compounds of this invention were also evaluated for insecticidal activity. They were especially active against insects of the order Lepidoptera.

TABLE 1

ACARICIDAL ACTIVITY

| Cmpd. of Ex. | Rate (ppm) | Exposure Time (Hr) | % Kill[1] TSM—R | TSM—S |
|---|---|---|---|---|
| 1 | 50 | 24 | 100 | |
|   | 100 | 48 | | 100 |
| 2 | 50 | 24 | | 100 |
|   | 100 | 48 | | 100 |
| 3 | 100 | 24 | | 26 |
|   | 100 | 48 | | 100 |
| 4 | 100 | 24 | | 10 |
|   | 100 | 48 | | 100 |
| 5 | 100 | 24 | | 0 |
|   | 100 | 48 | | 92 |
| 6 | 100 | 24 | | 11 |
|   | 100 | 48 | | 9 |
| 7 | 100 | 24 | | 0 |
|   | 100 | 48 | | 72 |
| 8 | 50 | 48 | | 100 |
| 9 | 100 | 24 | 100 | 70 |
|   | 100 | 48 | | 100 |
| 10 | 50 | | | 100 |
|   | 100 | 48 | | 100 |
| 11 | 50 | 24 | 100 | |
|   | 100 | 48 | | 100 |
| 12 | 100 | 24 | | 0 |
|   | 100 | 48 | | 51 |
| 13 | 100 | 24 | | 0 |
|   | 100 | 48 | | 0 |
| 14 | 800 | 24 | | 100 |
|   | 100 | 48 | | 0 |
| 15 | 100 | 24 | | 12 |
|   | 100 | 48 | | 2 |
| 16 | 100 | 24 | | 3 |
|   | 100 | 48 | | 98 |
| 17 | 100 | 24 | | 79 |
|   | 50 | 48 | | 100 |
| 18 | 100 | 24 | | 100 |
|   | 100 | 48 | | 100 |
| 19 | 100 | 24 | | 65 |
|   | 100 | 48 | | 31 |
| 20 | 100 | 24 | | 100 |
|   | 50 | 48 | | 100 |
| 21 | 100 | 24 | | 38 |
|   | 100 | 48 | | 91 |
| 22 | 100 | 24 | | 81 |
|   | 100 | 48 | | 100 |
| 23 | 100 | 24 | | 6 |
|   | 100 | 48 | | 8 |
| 24 | 100 | 24 | | 100 |
|   | 100 | 48 | | 100 |
| 25 | 100 | 24 | | 26 |
|   | 100 | 48 | | 100 |
| 26 | 100 | 24 | | 56 |
|   | 100 | 48 | | 96 |
| 27 | 100 | 24 | | 2 |
|   | 100 | 48 | | 6 |
| 28 | 100 | 24 | | 7 |
|   | 100 | 48 | | 100 |
| 29 | 100 | 24 | | 0 |
|   | 100 | 48 | | 79 |
| 36 | 25 | 24 | | 57 |
|   | 25 | 48 | | 100 |
| 37 | 100 | 24 | | 86 |
|   | 100 | 48 | | 100 |

[1]Acarid species
TSM = twospotted spider mite (*Tetranychus urticae*)
—R = Strain is resistant to phosphate insecticides
—S = Strain is not resistant to any types of insecticides

EXHIBIT B

| Cmpd. of Ex. | Rate (ppm) | Exposure Time (Hr) | % Kill TSM—S |
|---|---|---|---|

TABLE 1-continued

ACARICIDAL ACTIVITY

| | | | |
|---|---|---|---|
| 38 | 100 | 48 | 100 |
| 39 | 100 | 48 | 100 |
| 40 | 100 | 48 | 100 |
| 41 | 100 | 48 | 100 |
| 42 | 100 | 48 | 100 |
| 43 | 50 | 48 | 100 |
| 44 | 50 | 48 | 81 |
| 45 | 50 | 48 | 100 |
| 46 | 100 | 48 | 100 |
| 47 | 50 | 48 | 100 |
| 48 | 50 | 48 | 100 |
| 49 | 100 | 48 | 100 |
| 50 | 50 | 48 | 100 |
| 51 | 50 | 48 | 100 |
| 52 | 50 | 48 | 11 |
| 53 | 50 | 48 | 100 |
| 54 | 50 | 48 | 100 |
| 55 | 50 | 48 | 100 |
| 56 | 50 | 48 | 100 |
| 57 | 50 | 48 | 100 |
| 58 | 50 | 48 | 100 |
| 59 | 50 | 48 | 96 |
| 60 | 50 | 48 | 100 |
| 62 | 100 | 48 | 100 |
| 63 | | 48 | 100 |
| 64 | 100 | 48 | 100 |
| 65 | 100 | 48 | 100 |
| 66 | 100 | 48 | 100 |
| 67 | 100 | 48 | 100 |
| 68 | 100 | 48 | 100 |

What is claimed is:

1. A compound of the formula

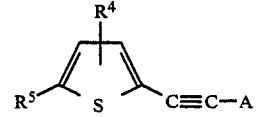

in which:
(a) $R^5$ is phenyl, $R^4$ is hydrogen, and A is selected from the group consisting of halophenyl, alkoxyphenyl, phenoxyphenyl, aminophenyl, alkylcarbonylaminophenyl, haloalkylcarbonylaminophenyl, haloalkoxyphenyl, halothienyl, alkoxycarbonylthienyl, haloalkoxyalkylphenyl, naphthyl, haloalkylphenyl, and (alkyl)halophenyl; or
(b) A is phenyl, $R^4$ is hydrogen or methyl and $R^5$ is selected from the group consisting of alkoxyphenyl, phenylethynylthienyl, haloalkylcarbonylthienyl, halophenyl, halothienyl, alkoxycarbonylthienyl, cycloalkyloxycarbonylthienyl, naphthyl and phenylethynyl;
(c) $R^5$ is 5-methylthienyl, $R^4$ is hydrogen and A is selected from the group consisting of haloalkylphenyl, formylphenyl, phenylcarbonylphenyl, alkylsulfonyloxyphenyl, alkylcarbonyloxyphenyl, alkylsulfonylphenyl, hydroxyphenyl, alkoxyphenyl and halophenyl;
(d) A is alkylphenyl or alkoxyphenyl, $R^4$ is hydrogen and $R^5$ is selected from the group consisting of alkylthiothienyl, alkylsulfinylthienyl, O,O-dialkylphosphorylthienyl, alkoxyphenylethynyl and alkoxycarbonylthienyl.

2. An acaricidal composition comprising an acaricidally effective amount of at least one compound of claim 1 in admixture with an agriculturally acceptable carrier.

3. A method for controlling acarids which comprises applying to the acarid, its habitat or plants upon which it feeds an acaricidally effective amount of at least one compound of claim 1.

4. The method of claim 3, employing the compound 1-(5-phenylthien-2-yl)-2-(4-methylphenyl)ethyne.

5. The method of claim 3, employing the compound 1-[5'-methyl(2,2'-bithien-5-yl)]-2-(4-chlorophenyl)ethyne.

* * * * *